(12) United States Patent
Brunelle et al.

(10) Patent No.: US 7,268,237 B2
(45) Date of Patent: Sep. 11, 2007

(54) DIRECT DIANHYDRIDE SYNTHESIS

(75) Inventors: Daniel Joseph Brunelle, Burnt Hills, NY (US); James Anthony Cella, Clifton Park, NY (US); Qing Ye, Schenectady, NY (US); Kwok Pong Chan, Troy, NY (US)

(73) Assignee: General Electric Company, Niskayuna, NY (US)

( * ) Notice: Subject to any disclaimer, the term of this patent is extended or adjusted under 35 U.S.C. 154(b) by 151 days.

(21) Appl. No.: 11/078,022

(22) Filed: Mar. 11, 2005

(65) Prior Publication Data

US 2006/0205958 A1 Sep. 14, 2006

(51) Int. Cl.
C07D 493/02 (2006.01)

(52) U.S. Cl. .................................... 549/241

(58) Field of Classification Search ................ 549/241
See application file for complete search history.

(56) References Cited

U.S. PATENT DOCUMENTS

| 3,850,964 | A | * | 11/1974 | Williams, III ............... 549/232 |
|---|---|---|---|---|
| 3,956,320 | A | | 5/1976 | Heath et al. |
| 4,257,953 | A | * | 3/1981 | Williams et al. ............ 548/461 |
| 4,273,712 | A | * | 6/1981 | Williams, III ............... 548/461 |
| 4,460,778 | A | * | 7/1984 | Brunelle ..................... 546/304 |
| 4,868,316 | A | | 9/1989 | Schwartz, Jr. |
| 5,081,298 | A | | 1/1992 | Brunelle |
| 5,082,968 | A | | 1/1992 | Brunelle |
| 5,132,423 | A | * | 7/1992 | Brunelle et al. ............. 544/162 |
| 6,469,224 | B1 | * | 10/2002 | Nobori et al. ............... 585/400 |
| 6,706,897 | B1 | | 3/2004 | Brunelle et al. |

OTHER PUBLICATIONS

U.S. Appl. No. 10/950,874, filed Sep. 24, 2004, entitled "Phosphazenium Salt Phase Transfer Catalysts", Daniel Joseph Brunelle et al.

* cited by examiner

Primary Examiner—D. Margaret Seaman
Assistant Examiner—Nizal S. Chandrakumar
(74) Attorney, Agent, or Firm—Andrew J. Caruso; William E. Powell, III

(57) ABSTRACT

This invention is related to a method for making diether dianhydrides by the reaction of halophthalic anhydride and a metal salt of an aromatic dihydroxy compound in the presence of a solvent and a phase transfer catalyst. Typical phase transfer catalyst include guanidium salts, aminopyridinium salts, or phosphazenium salts.

18 Claims, No Drawings

DIRECT DIANHYDRIDE SYNTHESIS

BACKGROUND

This invention relates to the preparation of diether dianhydrides, and more particularly to improved phase transfer catalyzed methods for such preparation.

Diether dianhydrides are important monomers for the preparation of polyetherimides having exceptionally high temperature performance and excellent solvent resistance. These properties are useful in high performance plastics applications such as advanced composites and electronic circuit materials.

A number of publications describe the preparation of diether dianhydrides, none however, discloses the method of the present invention and its advantages. Such publications include U.S. Pat. Nos. 3,956,320, 3,850,964, 4,868,316, and 6,706,897. Suitable reaction conditions for the reaction between halophthalic anhydrides and aromatic dihydroxy compounds include neat and solvent reactions and the presence of various catalysts, typically phase transfer catalysts such as tetraphenylphosphonium halides, fluorides such as potassium fluoride and cesium fluoride and carboxylic acids and their salts and hydrolysable esters. Many of these reactions suffer from low product yields. Moreover, numerous ambiguities are present in said publications regarding water content of the reaction mixtures and other conditions, making reproducibility questionable.

It is of interest, therefore, to provide a direct method for diether dianhydride preparation which affords high yields and a minimum of by-products, and which is consistently and reproducibly applicable.

BRIEF DESCRIPTION

The present invention provides an improved method for the preparation of diether dianhydrides through the use of substantially anhydrous solvent and at least one thermally stable phase transfer catalyst. In contrast with earlier methods, the method of the present invention consistently affords high yields of the desired product diether dianhydride and is highly reproducible.

In one embodiment the invention is a method for preparing a diether dianhydride which comprises contacting, under reactive and substantially anhydrous conditions, at least one halophthalic anhydride with at least one metal salt of an aromatic dihydroxy compound, in a nonpolar solvent in the presence of a thermally stable phase transfer catalyst.

In a typical embodiment, the invention provides a method for preparing an aromatic diether dianhydride of structure I,

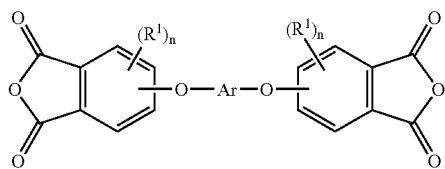

wherein Ar is a divalent aromatic radical; $R^1$ is independently at each occurrence a $C_1$-$C_{20}$ aliphatic radical, $C_3$-$C_{20}$ cycloaliphatic radical, or a $C_2$-$C_{20}$ aromatic radical; and n is an integer from 0 to 3 inclusive;

said method comprising contacting under reactive and substantially anhydrous conditions, a mixture comprising:

(a) at least one halophthalic anhydride of structure II

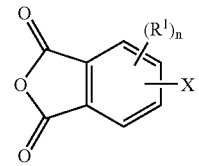

wherein $R^1$ is a $C_1$-$C_{20}$ aliphatic radical, $C_3$-$C_{20}$ a cycloaliphatic radical, or a $C_2$-$C_{20}$ aromatic radical; X is selected from the group consisting of chloro, fluoro, bromo, and iodo; and n is an integer ranging from 0 to 3 inclusive;

(b) at least one salt of an aromatic dihydroxy compound of structure III $$[^-OArO^-][M^{a+}]_{(2/a)} \qquad III$$

wherein Ar is a divalent aromatic radical; and M is independently at each occurrence an alkali metal cation, an alkaline earth metal cation, or a mixture thereof; and "a" is an integer having a value of 1 or 2;

(c) at least one aromatic solvent; and (d) at least one phase transfer catalyst selected from the group consisting of (i) guanidium salts having structure V

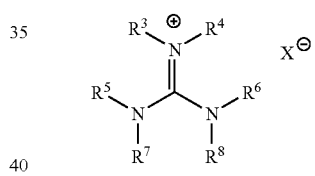

wherein $R^3$—$R^8$ are independently, at each occurrence a $C_1$-$C_{20}$ aliphatic radical, a $C_3$-$C_{20}$ cycloaliphatic radical, or a $C_2$-$C_{20}$ aromatic radical; and $X^-$ is an organic or inorganic anionic species;

(ii) aminopyridium salts having structure VI

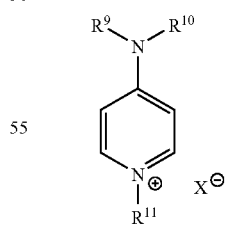

wherein $R^9$, $R^{10}$ and $R^{11}$ are independently at each occurrence a $C_1$-$C_{20}$ aliphatic radical, $C_3$-$C_{20}$ cycloaliphatic radical, $C_2$-$C_{20}$ aromatic radical, and wherein said $R^9$ and $R^{10}$ may be linked together form a cyclic structure comprising at least one nitrogen atom; and $X^-$ is an organic or inorganic anionic species, and (iii) phosphazenium salts having structure VII

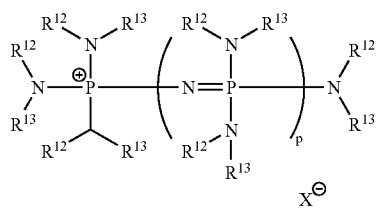

VII wherein $R^{12}$ and $R^{13}$ are independently at each occurrence a $C_1$-$C_{20}$ aliphatic radical, a $C_3$-$C_{20}$ cycloaliphatic radical, or a $C_2$-$C_{20}$ aromatic radical, or $R^{12}$ and $R^{13}$ may together form a cyclic structure comprising at least one nitrogen atom; and $X^-$ is an organic or inorganic anionic species.

DETAILED DESCRIPTION

The present invention may be understood more readily by reference to the following detailed description of preferred embodiments of the invention and the examples included therein. In the following specification and the claims which follow, reference will be made to a number of terms which shall be defined to have the following meanings.

The singular forms "a", "an" and "the" include plural referents unless the context clearly dictates otherwise.

"Optional" or "optionally" means that the subsequently described event or circumstance may or may not occur, and that the description includes instances where the event occurs and instances where it does not.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylpent-1-yl radical is a $C_6$ aliphatic radical comprising a methyl group, the methyl group being a functional group which is an alkyl group. Similarly, the 4-nitrobut-1-yl group is a $C_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl; difluorovinylidene; trichloromethyl, bromodichloromethyl, bromoethyl, 2-bromotrimethylene (e.g. —$CH_2CHBrCH_2$—), and the like. Further examples of aliphatic radicals include allyl, aminocarbonyl (i.e. —$CONH_2$), carbonyl, dicyanoisopropylidene (i.e. —$CH_2C(CN)_2CH_2$—), methyl (i.e. —$CH_3$), methylene (i.e. —$CH_2$—), ethyl, ethylene, formyl (i.e. —CHO), hexyl, hexamethylene, hydroxymethyl (i.e. —$CH_2OH$), mercaptomethyl (i.e. —$CH_2SH$), methylthio (i.e. —$SCH_3$), methylthiomethyl (i.e. —$CH_2SCH_3$), methoxy, methoxycarbonyl (i.e. $CH_3OCO$—), nitromethyl (i.e. —$CH_2NO_2$), thiocarbonyl, trimethylsilyl (i.e. $(CH_3)_3Si$—), t-butyldimethylsilyl, trimethoxysilylpropyl (i.e. $(CH_3O)_3SiCH_2CH_2CH_2$—), vinyl, vinylidene, and the like. By way of further example, a $C_1$-$C_{10}$ aliphatic radical contains at least one but no more than 10 carbon atoms. A methyl group (i.e. $CH_3$—) is an example of a $C_1$ aliphatic radical. A decyl group (i.e. $CH_3(CH_2)_9$—) is an example of a $C_{10}$ aliphatic radical.

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), anthracenyl groups (n=3) and the like. The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as trifluoromethylphenyl, hexafluoroisopropylidenebis(4-phen-1-yloxy) (i.e. —OPhC$(CF_3)_2$PhO—), chloromethylphenyl; 3-trifluorovinyl-2-thienyl; 3-trichloromethylphen-1-yl (i.e. 3-$CCl_3$Ph-), 4-(3-bromoprop-1-yl)phen-1-yl (i.e. $BrCH_2CH_2CH_2$Ph-), and the like. Further examples of aromatic radicals include 4-allyloxyphen-1-oxy, 4-aminophen-1-yl (i.e. $H_2NPh$-), 3-aminocarbonylphen-1-yl (i.e. $NH_2COPh$-), 4-benzoylphen-1-yl, dicyanoisopropylidenebis(4-phen-1-yloxy) (i.e. —OPhC$(CN)_2$PhO—), 3-methylphen-1-yl, methylenebis(phen-4-yloxy) (i.e. —OPh$CH_2$PhO—), 2-ethylphen-1-yl, phenylethenyl, 3-formyl-2-thienyl, 2-hexyl-5-furanyl; hexamethylene-1,6-bis(phen-4-yloxy) (i.e. —OPh$(CH_2)_6$PhO—); 4-hydroxymethylphen-1-yl (i.e. 4-HOCH$_2$Ph-), 4-mercaptomethylphen-1-yl (i.e. 4-HSCH$_2$Ph-), 4-methylthiophen-1-yl (i.e. 4-CH$_3$SPh-), 3-methoxyphen-1-yl, 2-methoxycarbonylphen-1-yloxy (e.g. methyl salicyl), 2-nitromethylphen-1-yl (i.e. -PhCH$_2$NO$_2$), 3-trimethylsilylphen-1-yl, 4-t-butyldimethylsilylphenl-1-yl, 4-vinylphen-1-yl, vinylidenebis(phenyl), and the like. The term "a $C_3$-$C_{10}$ aromatic radical" includes aromatic radicals containing at least three but no more than 10 carbon atoms. The aromatic radical 1-imidazolyl ($C_3H_2N_2$—) represents a $C_3$ aromatic radical. The benzyl radical ($C_7H_8$—) represents a $C_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group ($C_6H_{11}CH_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, halo alkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups and the like. For example, the 4-methylcyclopent-1-yl radical is a $C_6$ cycloaliphatic radical comprising a methyl group, the methyl group being a functional group which is an alkyl group. Similarly, the 2-nitrocyclobut-1-yl radical is a $C_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene2,2-bis (cyclohex-4-yl) (i.e. —$C_6H_{10}C(CF_3)_2$ $C_6H_{10}$—), 2-chloromethylcyclohex-1-yl; 3-difluoromethylenecyclohex-1-yl; 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. $CH_3CHBrCH_2C_6H_{10}$—), and the like. Further examples of cycloaliphatic radicals include 4-allyloxycyclohex-1-yl, 4-aminocyclohex-1-yl (i.e. $H_2NC_6H_{10}$—), 4-aminocarbonylcyclopent-1-yl (i.e. $NH_2COC_5H_8$—), 4-acetyloxycyclohex-1-yl, 2,2-dicyanoisopropylidenebis(cyclohex-4-yloxy) (i.e. —$OC_6H_{10}C(CN)_2C_6H_{10}O$—), 3-methylcyclohex-1-yl, methylenebis(cyclohex-4-yloxy) (i.e. —$OC_6H_{10}CH_2C_6H_{10}O$—), 1-ethylcyclobut-1-yl, cyclopropylethenyl, 3-formyl-2-terahydrofuranyl, 2-hexyl-5-tetrahydrofuranyl; hexamethylene-1,6-bis(cyclohex-4-yloxy) (i.e. —$OC_6H_{10}(CH_2)_6C_6H_{10}O$—); 4-hydroxymethylcyclohex-1-yl (i.e. 4-$HOCH_2C_6H_{10}$—), 4-mercaptomethylcyclohex-1-yl (i.e. 4-$HSCH_2C_6H_{10}$—), 4-methylthiocyclohex-1-yl (i.e. 4-$CH_3SC_6H_{10}$—), 4-methoxycyclohex-1-yl, 2-methoxycarbonylcyclohex-1-yloxy (2-$CH_3OCOC_6H_{10}O$—), 4-nitromethylcyclohex-1-yl (i.e. $NO_2CH_2C_6H_{10}$—), 3-trimethylsilylcyclohex-1-yl, 2-butyldimethylsilylcyclopent-1-yl, 4-trimethoxysilylethylcyclohex-1-yl (e.g. $(CH_3O)_3$ $SiCH_2CH_2C_6H_{10}$—), 4-vinylcyclohexen-1-yl, vinylidenebis (cyclohexyl), and the like. The term "a $C_3$-$C_{10}$ cycloaliphatic radical" includes cycloaliphatic radicals containing at least three but no more than 10 carbon atoms. The cycloaliphatic radical 2-tetrahydrofuranyl ($C_4H_7O$—) represents a $C_4$ cycloaliphatic radical. The cyclohexylmethyl radical ($C_6H_{11}CH_2$—) represents a $C_7$ cycloaliphatic radical.

As noted, the present invention provides a method for the preparation of diether dianhydrides of the formula I:

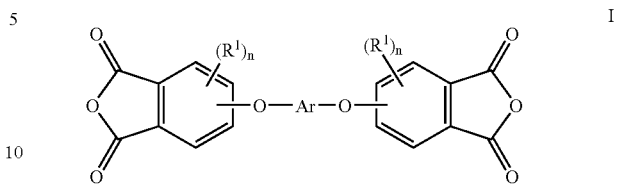

wherein Ar is a divalent aromatic radical; $R^1$ is independently at each occurrence a $C_1$-$C_{20}$ aliphatic radical, $C_3$-$C_{20}$ cycloaliphatic radical, or a $C_2$-$C_{20}$ aromatic radical; and n is an integer from 0 to 3 inclusive; said method comprising contacting, under reactive and substantially anhydrous conditions:

(a) at least one halophthalic anhydride of the formula II:

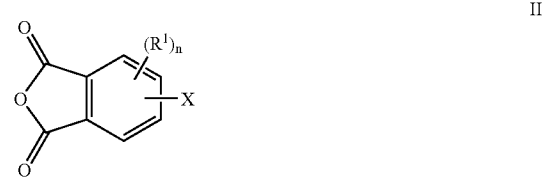

wherein $R^1$ is a $C_1$-$C_{20}$ aliphatic radical, a $C_3$-$C_{20}$ cycloaliphatic radical, or a $C_2$-$C_{20}$ aromatic radical; n is an integer from 0 to 3 inclusive; and X is a leaving group selected from the group consisting of fluoro, chloro, bromo, and iodo;

(b) at least one metal salt of an aromatic dihydroxy group of the formula III

wherein Ar is a divalent aromatic radical; and M is independently at each occurrence an alkali metal cation, an alkaline earth metal cation, or a mixture thereof; and "a" is an integer having a value of 1 or 2;

(c) at least one aromatic solvent; and (d) at least one thermally stable phase transfer catalyst.

Diether dianhydrides having structure I are exemplified by 2,2-bis[4-(3,4-dicarboxyphenoxy)phenyl]propane dianhydride (CAS Registry No. 38103-06-9); 2,2-bis[4-(2,3-dicarboxyphenoxy)phenyl]propane dianhydride; 2,2-bis[4-(3,4-dicarboxyphenoxy)phenyl]butane dianhydride; 1,1-bis[4-(3,4-dicarboxyphenoxy)phenyl]cyclohexane dianhydride; 1,1-bis[4-(3,4-dicarboxyphenoxy)phenyl]-3,3,5-trimethylcyclohexane dianhydride; 5,5'-[[1,1'-biphenyl]-4,4'-diylbis(oxy)]bis-1,3-isobenzofurandione (CAS Registry No. 26177-82-2).

Exemplary halophthalic anhydrides, as represented by formula II, include 3-chlorophthalic anhydride, 4-chlorophthalic anhydride, 3-fluorophthalic anhydride, 4-fluorophthalic anhydride, and combinations thereof.

The method of the present invention typically employs a salt of an aromatic dihydroxy compound, said salt having formula III

wherein Ar is a divalent aromatic radical, and M is independently at each occurrence an alkali metal cation, an alkaline earth metal cation, or a mixture thereof, and "a" is an integer having a value of 1 or 2. Salts having structure III are exemplified by hydroquinone disodium salt, resorcinol disodium salt, bisphenol A disodium salt, bisphenol A dipotassium salt, 4,4'-biphenol disodium salt, and the like.

The salt of the aromatic dihydroxy compound is typically derived from an aromatic dihydroxy compound having structure IV

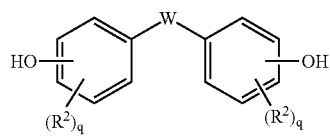

IV wherein $R^2$ is independently at each occurrence a halogen atom, a nitro group, a cyano group, a $C_1$-$C_{12}$ aliphatic radical, $C_3$-$C_{12}$ cycloaliphatic radical, or a $C_3$-$C_{12}$ aromatic radical; q is independently at each occurrence an integer from 0 to 4 inclusive; and W is a bond, O, S, SO, $SO_2$, Se, a $C_1$-$C_{20}$ aliphatic radical, $C_3$-$C_{20}$ cycloaliphatic radical, or a $C_3$-$C_{20}$ aromatic radical.

Dihydroxy aromatic compounds IV are exemplified by 3,4'-dihydroxydiphenylmethane; 4,4'-dihydroxybenzophenone; 4,4'-dihydroxydiphenylether; 2,2-bis(2-hydroxyphenyl)propane; bis-(2-hydroxyphenyl)methane; 2,2-bis(4-hydroxyphenyl)propane; 4,4'-dihydroxybiphenyl; 2,2-bis(4-hydroxy 2,6-dibromophenyl)propane, 2,4'-dihydroxybenzophenone; 4,4'-dihydroxydiphenylsulfone; 4,4'-dihydroxydiphenyl sulfoxide; 4,4'-dihydroxydiphenyl sulfide; and the like. Preferred aromatic dihydroxy compounds are bisphenol A (CAS Number: 80-05-7) and biphenol (CAS Number: 92-88-6).

The salt of the aromatic dihydroxy compound may be formed by contacting the aromatic dihydroxy represented by structure IV with at least one metal salt, such as a metal hydroxide, in a substantially anhydrous solvent. Typically, the at least one metal salt is employed such that the total amount of the at least one metal salt corresponds to at least one molar equivalent with respect to the number of hydroxyl groups present in the aromatic dihydroxy compound. When more than one metal salt is employed the metal salt of aromatic dihydroxy compound may comprise two or more different metal cations. It will be understood by those in the art that when the valency of the metal cation is greater than 1, one metal cation moiety may be bound to more than one oxygen in structure III. The salt of the aromatic dihydroxy compounds may be produced separately and added to the reaction mixture to make the diether dianhydride. In an alternate embodiment, the salt of the aromatic dihydroxy compound may be produced in situ in the reaction vessel used to make the diether dianhydride. Typically, the salt of the aromatic dihydroxy compound is prepared by contacting a metal hydroxide with a an aromatic dihydroxy compound. Suitble metal hydroxides include sodium hydroxide, potassium hydroxide, lithium hydroxide, cesium hydroxide, magnesium hydroxide, calcium hydroxide, aluminum hydroxide, combinations thereof, and the like.

The reaction to produce diether dianhydrides may be performed in the absence or in the presence of at least one solvent. In various embodiments it is preferred that the reaction be conducted in a solvent. While dipolar aprotic solvents may be used, their use is generally not advisable since they can promote side reactions and the formation of colored by-products. In various embodiments suitable solvents have a boiling point above about 120° C., preferably above about 150° C. and more preferably above about 180° C. Suitable solvents include, but are not limited to, ortho-dichlorobenzene (hereinafter "o-dichlorobenzene"), para-dichlorobenzene (hereinafter "p-dichlorobenzene"), 2,4-dichlorotoluene, 1,2,4-trichlorobenzene, diphenyl sulfone, phenetole, anisole, veratrole, and mixtures thereof. It is more preferred that chlorinated aromatic liquids be employed as solvents, examples of which include, but are not limited to, o-dichlorobenzene, 2,4-dichlorotoluene and 1,2,4-trichlorobenzene. o-Dichlorobenzene is often preferred since it is a high boiling liquid and thus, permits for the reaction to be run at higher temperatures and/or at superatmospheric pressures. The choice of o-dichlorobenzene as a solvent also allows for the use of a greater proportion of phase transfer catalyst in the reaction mixture. Such reaction conditions result in desirably higher reaction rates.

The reaction mixture should be substantially anhydrous, the term "substantially anhydrous" denoting a total water content of less than about 50 ppm, preferably less than about 20 ppm and most preferably less than about 10 ppm by weight. Any water present above this amount can inhibit the reaction, irrespective of its source. Traces of water may be present in either of the reagents, and they should be carefully removed by drying before beginning the reaction. Drying can be achieved by methods known in the art. Liquid reagents and solvents can be dried by distillation and/or by contact with molecular sieves, and solid materials by heating in an oven, most often under vacuum.

The thermally stable phase transfer catalysts (hereinafter referred to as "PTCs") are known in the art; reference is made, for example, to U.S. Pat. No. 5,081,298. By "thermally stable", it is meant that the phase transfer catalyst is of greater stability under the reaction conditions employed, than a tetraalkyl ammonium phase transfer catalyst such as tetrabutyl ammonium bromide. The thermally stable phase transfer cataylts used according to the method of the present invention are believed to possess greater stability with respect to olefin-forming elimination reactions (Sayseff and Hoffman type eliminations) and dealkylation than are the phase transfer catalysts comprising tetraalkyl ammonium moieties. Typical catalysts used according to the method of the present invention include hexaalkylguanidinium salts, pyridinium salts, phosphazenium salts and the like. Representative hexaalkylguanidinium salts are shown in formula V

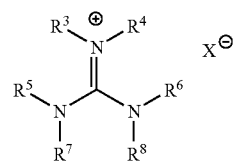

V wherein $R^3$—$R^8$ are independently, at each occurrence a $C_1$-$C_{20}$ aliphatic radical, a $C_3$-$C_{20}$ cycloaliphatic radical, or a $C_2$-$C_{20}$ aromatic radical; and $X^-$ is an organic or inorganic anionic species. Representative pyridnium salts suitable for use as phase transfer catalysts are shown in formula VI

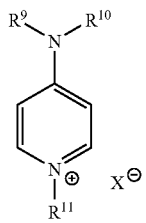

VI wherein $R^9$, $R^{10}$ and $R^{11}$ are independently at each occurrence a $C_1$-$C_{20}$ aliphatic radical, $C_3$-$C_{20}$ cycloaliphatic radical, $C_2$-$C_{20}$ aromatic radical, and wherein said $R^9$ and $R^{10}$ may be linked together form a cyclic structure comprising at least one nitrogen atom; and $X^-$ is an organic or inorganic anionic species. Representative phosphazenium catalysts are shown in formula VII

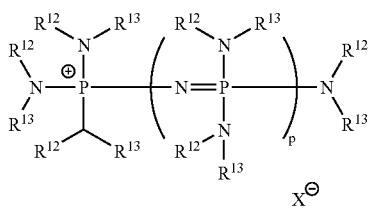

VII wherein $R^{12}$ and $R^{13}$ are independently at each occurrence a $C_1$-$C_{20}$ aliphatic radical, a $C_3$-$C_{20}$ cycloaliphatic radical, or a $C_2$-$C_{20}$ aromatic radical, or $R^{12}$ and $R^{13}$ may together form a cyclic structure comprising at least one nitrogen atom; and $X^-$ is an organic or inorganic anionic species. Suitable phase transfer catalysts are illustrated by 1-neopentyl-4-(N,N-dibutylamino)-pyridinium chloride, 1-neopentyl-4-piperidin-1-ylpyridinium chloride, 1-neopentyl-4-piperidin-1-ylpyridinium mesylate, 1-3-methylheptyl-4-(4-methyl)-piperidin-1-ylpyridinium chloride, hexaethylguanidinium chloride, dodecamethyl phosphazenium chloride, and the like.

The molar ratio of the two reactants, the halophthalic anhydride and the metal salt of an aromatic dihydroxy compound, is typically at least 2:1. In one embodiment the molar ratio of the two reactants, the halophthalic anhydride and the metal salt of an aromatic dihydroxy compound, is in the range of from about 2.1:1 to about 3.1:1. By way of illustration, a molar ratio of the two reactants, the halophthalic anhydride and the metal salt of an aromatic dihydroxy compound having a value of 2:1 refers to 2 moles of halophthalic anhydride per mole of the metal salt of an aromatic dihydroxy compound.

The amount of PTC used may be in the range of from about 0.2 mole percent to about 10 mole percent, with respect to the salt of the aromatic dihydroxy compound, more preferably in the range of from about 0.5 mole percent to about 2 mole percent.

When the reaction between the halophthalic anhydride and the metal salt of an aromatic dihydroxy compound is complete, the product diether dianhydride may be isolated by conventional techniques that are well known to those of ordinary skill in the art.

Without further elaboration, it is believed that one skilled in the art can, using the description herein, utilize the present invention to its fullest extent. The following examples are included to provide additional guidance to those skilled in the art in practicing the claimed invention. The examples provided are merely representative of the work that contributes to the teaching of the present application. Accordingly, these examples are not intended to limit the invention, as defined in the appended claims, in any manner.

EXAMPLES

All parts and percentages are by weight unless otherwise designated. Chemicals and solvents were reagent grade, and were carefully dried. Solvents were dried over activated 3 Å molecular sieves before use. Analysis was performed by contacting the reaction mixture with n-butylamine and acetic acid for at least 30 minutes to convert anhydrides to the corresponding N-(n-butyl)imides, followed by high pressure liquid chromatography using a tetrahydrofuran-water mixture as the eluting solvent.

Example 1

A dry 25 mL flask was charged with 403 mg (1.482 mmol) of the disodium salt of bisphenol A, 500 mg (3.012 mmol) of 4-fluorophthalic anhydride, 46 mg (0.148 mmol) of 4-(N,N-dibutylamino)-N-neopentylpyridinium chloride, 8.5 g (10% solids) of dry o-dichlorobenzene and 55 mg of o-terphenyl (internal standard). The flask was immersed in an oil bath maintained at 180° C. and the mixture was stirred magnetically. The temperature within the reaction flask was about 175° C. Samples (~0.1 mL) were withdrawn periodically dissolved in 6 mL of acetic acid and approximately. 0.5 mL of methylamine (40% aqueous soln.) and heated at 125-130° C. for 1.5 hours. These samples were analyzed for the bis N-methyl imide of bisphenol A dianhydride by liquid chromatography. By following the diether dianhydride formation in this manner it was determined that the yield of product bisphenol A dianhydride (BPADA) had reached 82% after one hour.

Example 2

The reaction of Example was was carried out on a slightly larger scale (6.09 mmol scale based on disodium salt of bisphenol A). The product isolated as follows. The hot reaction mixture (after one hour at approximately 175° C.) was filtered through Celite and the filtrate was steam distilled to remove o-dichlorobenzene and hydrolyze the anhydride moieties. The resulting aqueous suspension was made basic by addition of sodium carbonate, treated with activated charcoal and filtered through Celite. The filtrate was acidified by addition to cold hydrochloric acid and the product was extracted into ether. Evaporation of the ether extracts afforded 3.01 g (88.9%) of the tetracid as a white solid.

Example 3

A dry 100 mL flask was charged with 1.69 g (7.3 mmol) of the disodium salt of biphenol, 2.44 g, (146 mmol) of 4-fluorophthalic anhydride, 2 mL (14 mmol) of hexaethylguanidinium chloride as a 15 weight % solution in o-dichlorobenzene, and 44 g of dry o-dichlorobenzene. The flask was immersed in an oil bath maintained at 180° C. and the mixture was stirred magnetically. After 15 minutes, the reaction mixture was filtered hot to remove the sodium fluoride by-product. The filtrate was allowed to cool to room temperature and the product dianhydride crystallized from the solvent as a cream colored solid which was isolated by filtration (3.1 g, 90% yield).

Example 4

A dry 100 mL flask was charged with 2.0 g (7.3 mmol) of the disodium salt of bisphenol A, 2.67 g (14.6 mmol) of 4-chlorophthalic anhydride, 4 mL (14 mmol) of hexaethylguanidinium chloride as a 15 weight % solution in o-dichlorobenzene, 48 g of dry o-dichlorobenzene, and 100 mg of o-terphenyl (internal standard). The flask was immersed in an oil bath maintained at 180° C. and the mixture was stirred magnetically. The reaction was followed as in Example 1. The yield of biphenol dianhydride had reached 25% after 5 hours.

Example 5

A dry 100 mL flask was charged with 2.0 g (7.3 mmol) of the disodium bisphenol A, 2.67 g (14.6 mmol) of 3-chlorophthalic anhydride, 4 mL (14 mmol) of hexaethylguanidinium chloride as a 15 weight % solution in o-dichlorobenzene, 48 g of dry o-dichlorobenzene, and 100 mg of o-terphenyl (internal standard). The flask was immersed in an oil bath maintained at 180° C. and the mixture was stirred magnetically. The reaction was followed as in Example 1. The yield of bisphenol A dianhydride had reached 40% after 2 hour.

Table 1 shows the effect of the catalyst used, catalyst concentration and the % solids content in the reaction mixture on the final yield of the product dianhydride.

TABLE 1

| Exp. No. | Metal counter ion | Time (h) | Temp. (° C.) | Conc. (% solid) | Catayst* | Conc. Catalyst (mole %) | Yield (%) |
|---|---|---|---|---|---|---|---|
| 1 | Na | 2.0 | 175 | 10 | none | 0 | 2 |
| 2 | Na | 2.0 | 175 | 10 | Bu$_4$NBr | 10 | 2 |
| 3 | Na | 0.3 | 175 | 10 | 9a | 10 | 90 |
| 4 | Na | 4.0 | 175 | 10 | 9a | 0.5 | 85 |
| 5 | Na | 1.0 | 175 | 10 | 7a | 5 | 82 |
| 6 | Na | 0.5 | 175 | 10 | 7a | 10 | 88 |
| 7 | Na | 0.5 | 175 | 30 | 7a | 10 | 60 |
| 8 | Na | 0.5 | 175 | 40 | 7a | 10 | 55 |
| 9 | Na | 1.0 | 175 | 10 | 7b | 10 | 75 |
| 10 | Na | 1.0 | 175 | 10 | 7c | 10 | 75 |
| 11 | Na | 1.0 | 175 | 10 | 8 | 10 | 82 |
| 12 | K | 2.5 | 175 | 9 | 7a | 5 | 38 |
| 13 | K | 2.5 | 175 | 9 | 7b | 5 | 37 |
| 14 | K | 5.5 | 175 | 10 | 7a | 10 | 75 |

*Bu$_4$NBr: Tetrabutyl ammonium bromide
7a: 1-neopentyl-4-(N,N-dibutylamino)-pyridinium chloride
7b: 1-neopentyl-4-piperidin-1-ylpyridinium chloride
7c: 1-neopentyl-4-piperidin-1-ylpyridinium mesylate
8: 1-3-methylheptyl-4-(4-methyl)-piperidin-1-ylpyridinium chloride
9a: Hexaethylguanidinium chloride While only certain features of the invention have been illustrated and described herein, many modifications and changes will occur to those skilled in the art. It is, therefore, to be understood that the appended claims are intended to cover all such modifications and changes as fall within the true spirit of the invention.

What is claimed is:

1. A method for preparing an symmetrical aromatic diether dianhydride of structure I,

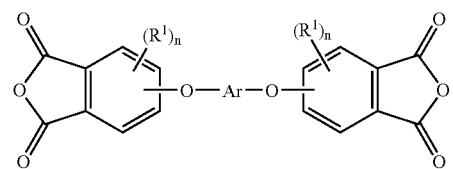

wherein Ar is a divalent aromatic radical; R$^1$ is a C$_1$-C$_6$, aliphatic radical, C$_3$-C$_6$ cycloaliphatic radical; and n=1;
said method comprising contacting under reactive and substantially anhydrous conditions, a mixture comprising:
at least one halophthalic anbydride of structure II

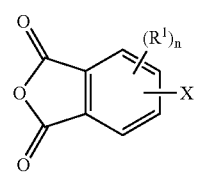

wherein R$^1$ is a C$_1$-C$_6$, aliphatic radical, C$_3$-C$_6$ a cycloaliphatic radical;
X is selected from the group consisting of chloro, fluoro, bromo, and iodo; and n=1;
at least one salt of an aromatic dibydroxy compound, said salt having structure III

[⁻OArO⁻][M$^{a+}$]$_{(2/a)}$   III wherein Ar is a divalent aromatic radical; and M is independently at each occurrence an alkali metal cation, an alkaline earth metal cation, or a mixture thereof; and "a" is an integer having a value of 1 or 2;
at least one solvent selected from the group consisting of ortho-dichlorobenzen, para-dichlorobenzene, dichlorotoluene, 2,4-dichiorotoluene, 1,2,4-trichlorobenzene, diphenyl sulfone, phenetole, anisole, veratrole,
at least one phase transfer catalyst selected from the group consisting of:
guanidium salts having structure V

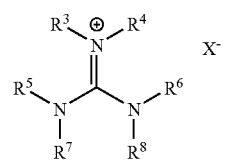

wherein R$^3$-R$^8$ are independently, at each occurrence a C$_1$-C$_6$, aliphatic radical, a C$_3$-C$_6$ cycloaliphatic radical, or and X$^-$ is an organic or inorganic anionic species, (ii) aminopyridium salts having structure VI

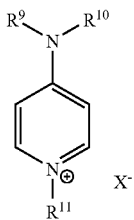

wherein $R^9$, $R^{10}$ and $R^{11}$ are independently at each occurrence a $C_1$-$C_6$, aliphatic radical, $C_3$-$C_6$ cycloaliphatic radical, and wherein said $R^9$ and $R^{10}$ may be linked together form a cyclic structure comprising at least one nitrogen atom; and X⁻ is an organic or inorganic anionic species, wherein $R^{12}$ and $R^{13}$ are independently at each occurrence a $C_1$-$C_{20}$ aliphatic radical, a $C_3$-$C_{20}$ cycloaliphatic radical, or a $C_2$-$C_{20}$ aromatic radical, or $R^{12}$ and $R^{13}$ may together form a cyclic structure comprising at least one nitrogen atom; and X⁻ is an organic or inorganic anionic species; p is an integer ranging from 1 to 3.

2. The method according to claim 1 wherein the halophthalic anhydride is selected from the group consisting of 3-chlorophthalic anhydride, 4-chlorophthalic anhydride, 3-fluorophthalic anhydride, 4-fluorophthalic anhydride, and a mixture thereof.

3. The method according to claim 1 wherein M is sodium or potassium.

4. The method according to claim 1 wherein said aromatic dihydroxy compound is selected from the group consisting of bisphenols having structure IV

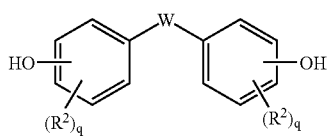

wherein $R^2$ is a halogen atom, a nitro group, a cyano group, a $C_1$-$C_6$, aliphatic radical, $C_3$-$C_6$ cycloaliphatic radical, or a; and W is a bond, O, S, SO, $SO_2$, Se, a $C_1$-$C_6$, aliphatic radical, $C_3$-$C_{20}$ cycloaliphatic radical.

5. The method according to claim 1 wherein said aromatic dihydroxy compound is selected from the group consisting of 4,4'-biphenol, and bisphenol A.

6. The method according to claim 1 wherein the phase transfer catalyst is hexaethylguanidinium chloride.

7. The method according to claim 1 wherein a proportion of phase transfer catalyst in a range from about 0.2 mole percent to about 10.0 mole percent based on halophthalic anhydride is employed.

8. The method according to claim 1 wherein said contacting comprises heating at a temperature in a range from about 150° C. to about 300° C.

9. The method according to claim 8 wherein a temperature in a range from about 170 to about 250° C. is employed.

10. The method according to claim 8 wherein a temperature in a range from about 180 to about 200° C. is employed.

11. The method according to claim 1 wherein the reaction is conducted at atmospheric pressure.

12. The method according to claim 1 wherein said solvent comprises less than 20 ppm water.

13. The method according to claim 1 wherein said solvent comprises less than 5 ppm water.

14. A method for preparing a diether and dianhydride I,

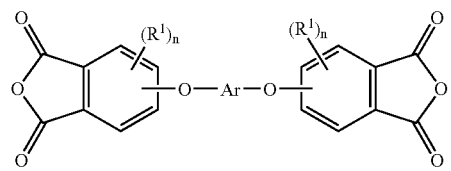

wherein Ar is a divalent aromatic radical; $R^1$ is a $C_1$-$C_6$, aliphatic radical, a $C_3$-$C_6$ cycloaliphatic radical, and n=1;
said method comprising contacting a mixture comprising 3-fluorophthalic anhydride and 4-fluorophthalic anhydride, with at least one salt of an aromatic dihydroxy compound of structure III

[⁻OArO⁻][$M^{a+}$]$_{(2/a)}$     III wherein Ar is a divalent aromatic radical; and M is independently at each occurrence an alkali metal cation, an alkaline earth metal cation, or a mixture thereof, and "a" is an integer having a value of 1 or 2;
said contacting being carried out in the presence of a solvent selected from the group consisting of ortho-dichlorobenzene, para-dichlorobenzene, dichlorotoluene, 2,4-dichlorotoluene, 1,2,4-trichlorobenzene, diphenyl sulfone, phenetole, anisole, veratrole, a phase transfer catalyst under substantially anhydrous conditions at a temperature in a range from about 150 to about 300° C., said solvent having a boiling point greater than about 150° C., said phase transfer catalyst being selected from the group consisting of hexalkylguanidinium salts.

15. The method according to claim 14 wherein said phase transfer catalyst is hexaethylgnauidinium chloride.

16. A method for preparing a diether symmetrical dianhydride I,

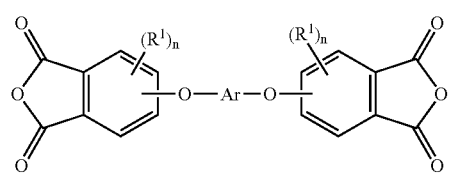

wherein Ar is a divalent aromatic radical, $R^1$ is independently at each occurrence a $C_1$-$C_6$, aliphatic radical, a $C_3$-$C_6$ cycloaliphatic radical, and n=1;
said method comprising contacting a mixture comprising 3-chlorophthalic anhydride and 4-chlorophthalic anhydride, with at least one salt of an aromatic dihydroxy compound of structure III

[⁻OArO⁻][$M^{a+}$]$_{(2/a)}$     III wherein Ar is a divalent aromatic radical, and M is independently at each occurrence an alkali metal cation, an alkaline earth metal cation, or a mixture thereof; "a" is an integer having a value of 1 or 2;
said contacting being carried out in the presence of a solvent selected from the group consisting of ortho-dichlorobenzene, para-dichlorobenzene, dichlorotoluene, 2,4-dichlorotoluene, 1,2,4-trichlorobenzene, dipheuyl sulfone, phenetole, anisole, veratrole, a phase transfer catalyst under substantially anhydrous conditions at a temperature in a range from about 150 to about 300° C., said solvent having a boiling point greater than about 150° C., said phase transfer catalyst being selected from the group consisting of hexalkylguanidinium salts.

17. The method according to claim 16 wherein said phase transfer catalyst is hexaethylguanidinium chloride 18. A method for preparing a diether symmetrically dianhydride I,

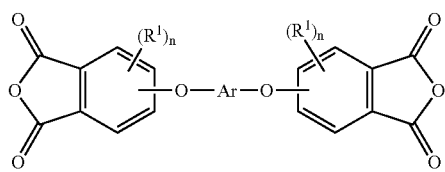

wherein Ar is a divalent aromatic radical, $R^1$ is a $C_1$-$C_6$, aliphatic radical, a $C_3$-$C_6$ cycloaliphatic radical, and n=1;

said method comprising contacting a mixture comprising 3-chlorophtbalic anhydride and 4-chlorophthalic anbydride, with at least one salt of an aromatic dihydroxy compound of structure III

wherein Ar is a divalent aromatic radical; and M is independently at each occurrence an alkali metal cation, an alkaline earth metal cation, or a mixture thereof; "a" is an integer having a value of 1 or 2;

said contacting being carried out in the presence of a solvent selected from the aroup consisting of ortho-dichlorobenzene, para-dichtorobenzene, dichlorotoluene, 2,4-dichiorotoluene, 1,2,4-trichlorobenzene, diphenyl sulfone, phenetole, anisole, veratrole, a phase transfer catalyst under substantially aub.yclxous conditions at a temperature in a range from about 150 to about 300° C., said solvent having a boiling point greater than about 150° C., said phase transfer catalyst being selected from the group consisting of hexaethylguanidinium chloride, 1-neopentyl-4-(N,N-dibutylaniino)-pyridinium chloride, 1-neopentyl-4-piperidin-1-ylpyridinium chloride, 1-neopenryl-4-piperidin-1-ylpyridinium mesylate, 1-3-methylheptyl-4-(4-methyl)-piperidin-1-ylpyridinium chloride, and combinations thereof.

* * * * *